(12) United States Patent
McMichael (10) Patent No.: US 6,578,582 B2
(45) Date of Patent: Jun. 17, 2003

(54) METHOD AND APPARATUS USING IDS™ FOR MULTI-AGENT THERAPY

(75) Inventor: John P. McMichael, Wexford, PA (US)

(73) Assignee: The RxFiles Corporation, Nokomis, FL (US)

( * ) Notice: Subject to any disclaimer, the term of this patent is extended or adjusted under 35 U.S.C. 154(b) by 82 days.

(21) Appl. No.: 09/939,056

(22) Filed: Aug. 24, 2001

(65) Prior Publication Data

US 2003/0051736 A1 Mar. 20, 2003

(51) Int. Cl.⁷ .............................................. A61B 19/00
(52) U.S. Cl. ...................................... 128/898; 600/300
(58) Field of Search .................... 128/897–98; 600/300, 600/308, 347, 364–66, 368

(56) References Cited

U.S. PATENT DOCUMENTS

| | | | | |
|---|---|---|---|---|
| 5,365,948 A | * | 11/1994 | McMichael | 128/898 |
| 5,542,436 A | * | 8/1996 | McMichael | 128/897 |
| 5,694,950 A | * | 12/1997 | McMichael | 128/898 |
| 6,267,116 B1 | * | 7/2001 | McMichael | 128/898 |

* cited by examiner

Primary Examiner—John P. Lacyk
(74) Attorney, Agent, or Firm—Gifford, Krass, Groh, Sprinkle, Anderson & Citkowski, P.C.

(57) ABSTRACT

A method and apparatus using IDS™ technology to calculate new agent doses in a multi-agent therapy. The overall proportion of each agent is determined by the amount of agent as it relates to the dosing range. The overall proportion as well as the intrinsic potency of the agent is used to determine the total proportional effect which each agent has on the surrogate marker. This parameter is then inserted into the four-parameter equation for calculating dose by adjusting the proportional change in marker that is attributed to the activity of the agent.

12 Claims, 2 Drawing Sheets

METHOD AND APPARATUS USING IDS™ FOR MULTI-AGENT THERAPY

This document may contain material which is the subject of copyright protection. All rights in such copyrightable material are hereby reserved.

FIELD OF THE INVENTION

The present invention relates generally to a method and apparatus using IDS™ (Intelligent Dosing System™) technology for multi-agent therapy. More particularly, the present invention relates to a method and apparatus for use in treating a patient with multiple agents to optimize therapy and to prevent an adverse response. The present invention can utilize either biological substance levels or other surrogate markers to determine the effectiveness of the dosing regimen and, if necessary, to suggest a new more optimal regimen.

The term "agent" as used herein includes, but is not limited to: vaccines; serums; drugs; adjuvants to enhance or modulate a resulting immune response; vitamin antagonists; medications; autologous whole-cell vaccines (using cells derived from a patient's own tumor); allogenic whole-cell vaccines (using cancer cell lines established in vitro and then used to vaccinate multiple patients); tumor specific antigen/tumor associated antigen (TSA/TAA) based vaccines and hormonal autoimmunization approaches; all other cancer vaccines; Melacine; CancerVax; immune-boosting interferon; peptides; dendritic cells having melanoma protein thereon; interleukin-12; substances which stimulate or energize blood cells known as CD8 T cells; genes which make interleukin-12; tumor cells weakened by genes which make interleukin-12; substances which block blood-vessel formation to prevent growth of tumors; immunized cells; recombinant subunit vaccines; DNA vaccines; live recombinant viral vector vaccines; live recombinant bacterial vector vaccines; live-attenuated vaccines; whole-inactivated vaccines; virus-like particle vaccines; synthetic peptide vaccines; "Jennerian" vaccines; complex vaccines; and combinations of two or more of the foregoing.

The term "surrogate marker" as used herein means all surrogate markers and includes, but is not limited to: a measurement of biological activity within the body which indirectly indicates the effect of treatment on a disease state or on any condition being treated; and any measurement taken on a patient which relates to the patient's response to an intervention, such as the intervention of a biological substance introduced into or on the patient. For example, CD4 cell counts and viral load are examples of surrogate markers in HIV infection.

BACKGROUND OF THE INVENTION

When a patient begins taking an agent or any medication for a length of time, a titration of the amount of agent taken by the patient is necessary in order to achieve the optimal benefit of the agent, and at the same time to prevent any undesirable side effects that taking too much of the agent could produce. Thus, there is a continuous balance between taking enough of the agent in order to gain the benefits from that agent, and at the same time not taking so much agent as to illicit a toxic event.

There is large inter-individual variability in the patient biological interactions and/or the patient pharmocodynamic and pharmacokinetic interactions of agents. What may be an appropriate agent dose for one individual, may be too much or too little for another. A physician was required to estimate the correct agent dosage for a patient and then to experiment with that dosage, usually by trial and error, until the correct dosage was achieved. Likewise, the FDA labeling of a agent suggests dosages based on epidemiological studies and again does not account for inter-individual variability. Non-linear least squares modeling methods involve the use of large amounts of data relating to a general population in order to calculate a best fit. Much like linear regression models, this method cannot take into account the variability between people with the same population characteristics.

Bayesian analysis is another method used to relate agent dose to efficacy. This method employs large-scale population parameters to stratify a population in order to better characterize the individuals. This method does not take into account the changes that can occur within a person over time, and as a result cannot reliably estimate dosages.

Pharmacokinetic compartment modeling has had success with some agents, but because the models are static and cannot adapt themselves to changes within a population or a patient, they are once again undesirable for dynamically determining agent dosages.

Expert systems have been developed using similar technology to predict specific drug dosages for specific immunosuppressant drugs (see, e.g., U.S. Pat. Nos. 5,365,948, 5,542,436 and 5,694,950). These algorithms, however, are not generic and only use immunosuppressant blood levels. Each algorithm is specific to an individual specific immunosuppressant drug. As it stands, these inventions cannot be applied to other agents and do not have a non-linear feedback loop mechanism.

Applicant's U.S. Pat. No. 6,267,116 discloses a major breakthrough in IDS™ technology, but can only accommodate one drug at a time.

It is a desideratum of the present invention to avoid the animadversions of conventional systems and techniques

SUMMARY OF THE INVENTION

The present invention provides in one embodiment thereof a method of calculating the next best dose for each agent of a multi-agent therapy which a patient may be using, comprising the steps of: accepting as first inputs the patient's current doses of a plurality of agents which the patient may be using; accepting as second inputs one or more numerical markers indicating one or more responses of the patient; and calculating new agent doses for said plurality of agents as a function of said first inputs, said second inputs, and contributions which each agent makes to an overall effect to be achieved by said multi-agent therapy.

The present invention provides in a further embodiment thereof a storage device having stored thereon an ordered set of instructions which, when executed by a computer, performs a predetermined method, comprising: first means for accepting as first inputs a patient's current doses of a plurality of agents which the patient may be using; second means for accepting as second inputs one or more numerical markers indicating one or more responses of the patient; and third means for calculating new agent doses for said plurality of agents as a function of said first inputs, said second inputs, and contributions which each agent makes to an overall effect to be achieved by said multi-agent therapy.

The present invention provides in another embodiment thereof an apparatus for calculating the next best dose for each agent of a multi-agent therapy which a patient may be using, comprising: first means for accepting as first inputs the patient's current doses of a plurality of agents which the patient may be using; second means for accepting as second inputs one or more numerical markers indicating one or more responses of the patient; and third means for calculating new agent doses for said plurality of agents as a function of said first inputs, said second inputs, and contributions which each agent makes to an overall effect to be achieved by said multi-agent therapy.

DETAILED DESCRIPTION OF THE INVENTION

Figure 1:
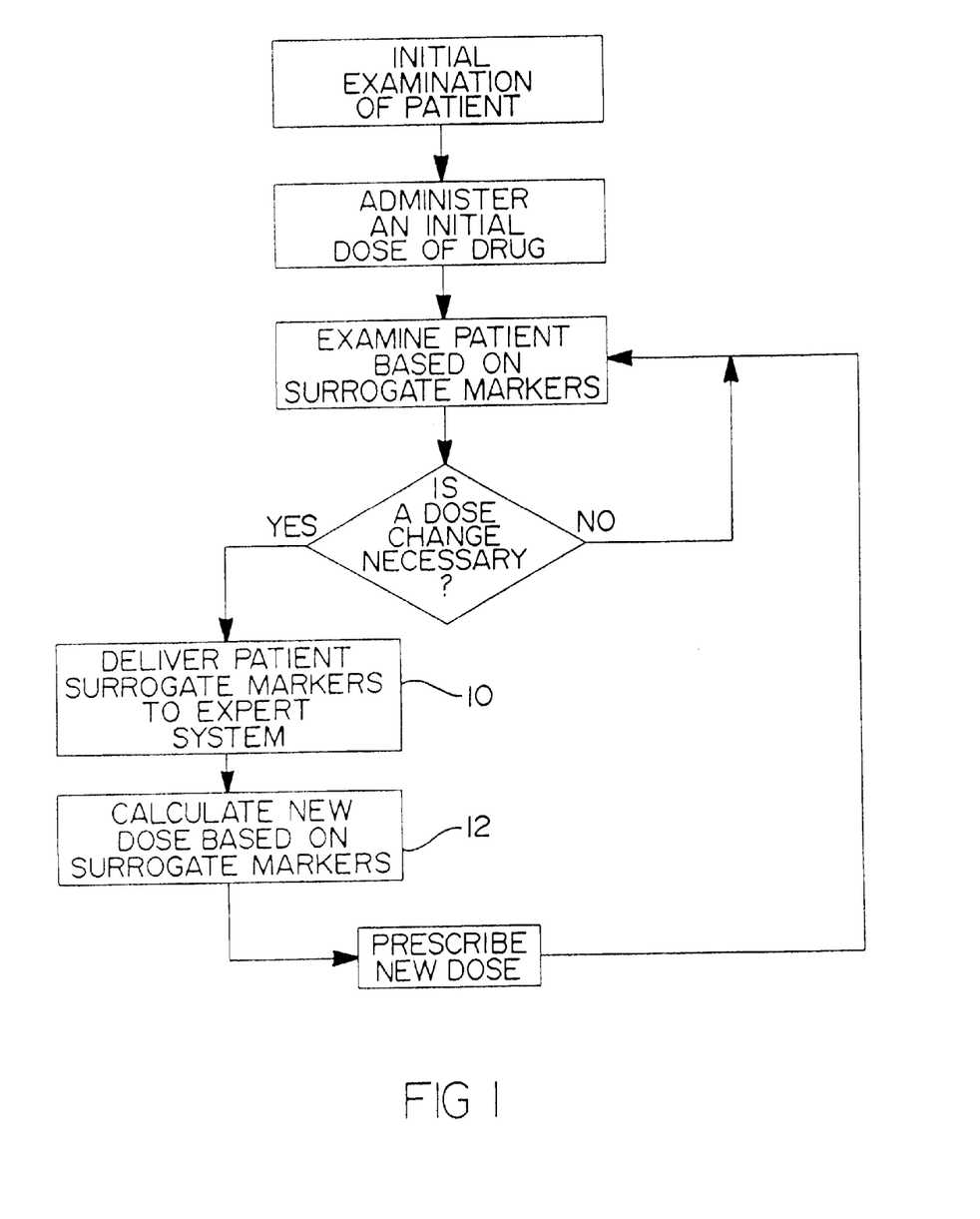
FIG. 1 shows a flow chart of the process by which new doses of an agent, of a multi-agent therapy, are determined according to a portion of the method of the invention.

FIG. 1 shows a flow chart of a portion of the overall process of treating a patient using this expert system. The actual expert system performs many steps which are described herein, whereas only the steps shown in blocks 10 and 12 are generally indicated the flow chart.

Figure 2:
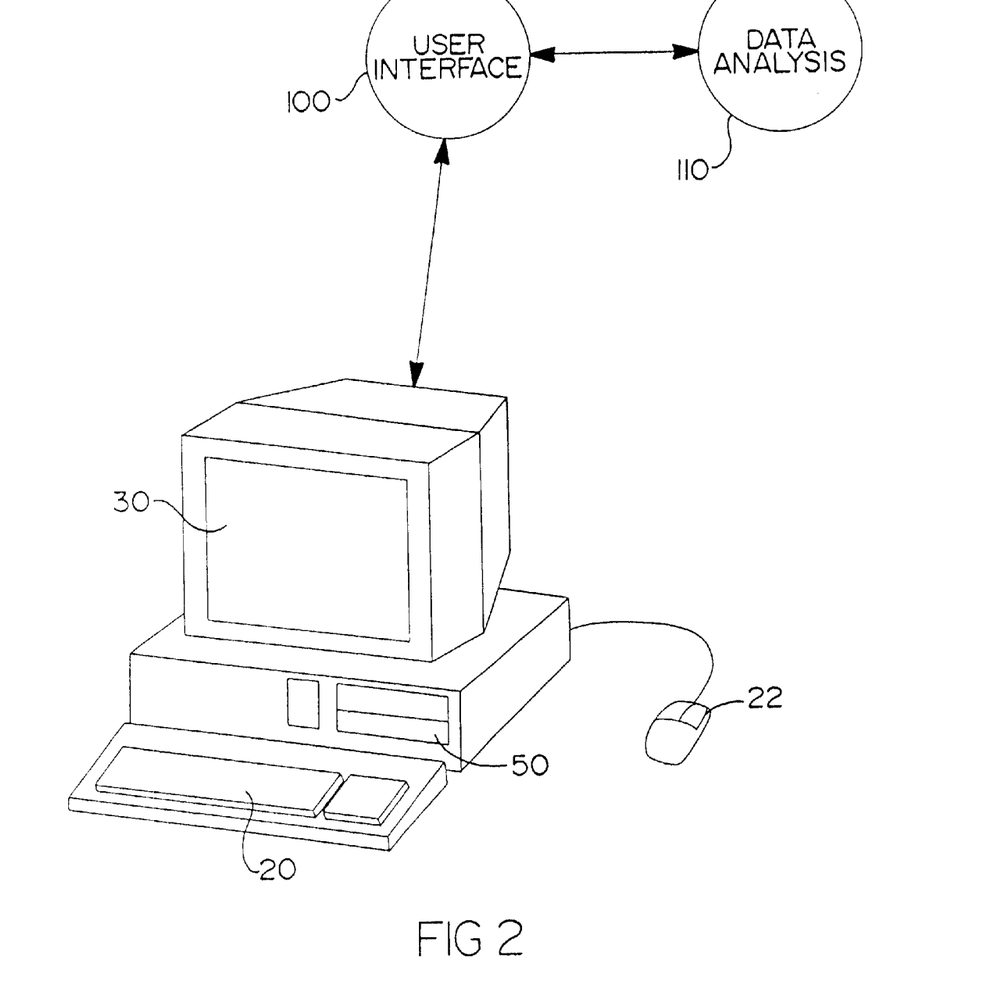
FIG. 2 shows an apparatus for use in calculating new doses of a plurality of agents used in a multi-agent therapy according to the invention.

This expert system includes a general purpose computer, shown in FIG. 2, comprising an input means, preferably a keyboard 20 and/or a mouse 22, an output means 30, preferably a video display screen, a data storage means 50, preferably a hard disk drive, and a processor. The expert computer program receives input data from a physician regarding the patient's current agent dose, the maximal dose range for that particular agent, and the percent response of the patient based on the surrogate markers used to monitor that agent.

Also characterized is the patient's response to the last dosing cycle as well as a dose response constant. This allows the expert system to individualize the patient dosing based on the patient's individual response to that particular agent. The system calculates a revised dosage based on the data input by the physician.

The software portion of the invention includes a user interface portion 100 to receive the input data and to output the revised dosage information, and a data analysis portion 110, which calculates the new dosage information based on the input data.

A physician prescribes a agent for a patient based on the FDA recommended dose on the label of the agent. The physician then re-evaluates the patient, usually daily, either in person or remotely depending on the agent being prescribed.

During the subsequent evaluations by the physician, the surrogate markers are monitored and sequentially compared to determine if there are, any toxicities associated with the agent. Also the numerical markers will be evaluated to see if the desired effect of the agent is being achieved.

Given the effectiveness of the agent's action relative to the surrogate markers, a change in agent dose is calculated by the system. Conversely, by employing this system, one could determine the expected result of the agent dose change on the surrogate marker.

The present invention will now be described in detail with respect to 2-agent IDS™ therapy and 3-agent IDS™ therapy, although it is applicable to any number of agents.

Using the IDS™ With Multi-agent (2 Agents) Therapy

When using a multi-agent regimen to treat patients it is necessary to calculate the next best dose for each agent the patient is using. The IDS™ technology in the form disclosed in applicant's U.S. Pat. No. 6,267,116 can only dose one agent at a time. The following calculations show how to use the concept, of the IDS™ and the dose response methodology to perform multiple computations, each based on the proportional response which a particular agent has on the overall response that is to be achieved.

The concept underlying this multi-agent dosing model is that each agent has some contribution to the overall effect. This contribution is determined by the amount of each agent the patient is using as well as the intrinsic potency of each agent. The overall proportion of each agent is determined by the amount of agent as it relates to the dosing range. The overall proportion as well as the intrinsic potency of the agent is used determine the total proportional effect which each agent has on the surrogate marker. This parameter (FOE1 or FOE2) is then inserted into the four-parameter equation (AND) for calculating dose by adjusting the proportional change in marker that is attributed to the activity of the agent.

To Calculate the First Agent $$NAD1=CAD1-\{[<(DANM1-CANM1)\times FOE1/CANM1>/<1+(CAD1/HIGH1)>]\times CAD1\}+LV1$$

To Calculate the Second Agent $$NAD2=CAD2-\{[<(DANM2-CANM2)\times FOE2>/<1+(CAD2/HIGH2)>]\times CAD2\}+LV2$$

where:

$$EANM1=\{[(CAD1-PAD1)/PAD1]\times[1+(PAD1/HIGH1)]\times PADM1\}+PADM1$$

$$EANM2=\{[(CAD2-PAD2)/PAD2]\times[1+(PAD2/HIGH2)]\times EANM1\}+EANM1$$

if CANM1<DANM1 and EANM2>CANM1, or if CANM1>DANM1 and EANM2<CANM1, then $$LV1=RESPONSE1\times CAD1\times(EANM2-CANM1)/CANM1/[1.3^{\cdot}(CAD1/HIGH1)]$$

if CANM1<DANM1 and EANM2<CANM1, or if CANM1>DANM1 and EANM2>CANM1, then $$LV1=-[RESPONSE1\times CAD1\times(CANM1-EANM2)/CANM1]/[1.3^{\cdot}(CAD/HIGH)]$$

if CANM2<DANM2 and EANM2>CANM2, or if CANM2>DANM2 and EANM2<CANM2, then $$LV2=RESPONSE2\times CAD2\times(EANM2-CANM2)/CANM2/[1.3^{\cdot}(CAD2/HIGH2)]$$

if CANM2<DANM2 and EANM2<CANM2, or if CANM2>DANM2 and EANM2>CANM2, then $$LV2 = -[RESPONSE2 \times CAD2 \times (CANM2 - EANM2)/CANM2]/[1.3^{\wedge}(CAD2/HIGH2)]$$

PAD1=Previous agent dose of the first agent
PAD2=Previous agent dose of the second agent
CAD1=Current agent dose of the first agent
CAD2=Current agent dose of the second agent
NAD1=New agent dose of the first agent
NAD2=New agent dose of the second agent
PADM1=Previous agent numerical marker for the first agent
CANM1=Current agent numerical marker for the first agent
CANM2=Current agent numerical marker for the second agent
DANM1=Desired agent numerical marker for the first agent
DANM2=Desired agent numerical marker for the second agent
FOE1=Factor of effect the first agent has on its associated numerical marker
FOE2=Factor of effect the second agent has on its associated numerical marker
HIGH1=The input parameter that is the high dose range for the first agent
HIGH2=The input parameter that is the high dose range for the second agent
RESPONSE1=Percent of total dose available for individualizing patient dose of the first agent
RESPONSE2=Percent of total dose available for individualizing patient dose of the second agent
1.3^(CAD1/HIGH1)=1.3 raised to an exponent of (CAD1/HIGH1)
1.3^(CAD2/HIGH2)=1.3 raised to an exponent of (CAD2/HIGH2)

To Calculate the Proportion of Effect Based on the Amount of Agent and the Agent's Intrinsic Effect Agent1 Effect=1
Agent2 Effect=1

$$Agent1 \text{ Proportion} = \frac{Dose1/Range1}{(Dose1/Range1 + Dose2/Range2)}$$

$$Agent2 \text{ Proportion} = \frac{Dose2/Range2}{(Dose1/Range1 + Dose2/Range2)}$$

Total Proportional $Effect1 =$ $$\frac{Dose1/Range1}{(Dose1/Range1 + Dose2/Range2)} \times Agent1 \text{ Effect}$$

Total Proportional $Effect2 =$ $$\frac{Dose2/Range2}{(Dose1/Range1 + Dose2/Range2)} \times Agent2 \text{ Effect}$$

$$FOE1 = \frac{\text{Total Proportional } Effect1}{\text{Total Proportional } Effect1 + \text{Total Proportional } Effect2}$$

$$FOE2 = \frac{\text{Total Proportional } Effect2}{\text{Total Proportional } Effect1 + \text{Total Proportional } Effect2}$$

EXAMPLE

Gemzar Dose is 5000
Taxol Dose is 250
Assume both agents have an equal effect.
Current Marker (ANC) is 0.5
Desired Marker (ANC) is 1.8

$$\text{Taxol Proportion} = \frac{250/50}{(250/500 + 5000/3300)} = \frac{0.5}{2.0152} = 0.2481$$

$$\text{Gemzar Proportion} = \frac{5000/3300}{(250/500 + 5000/3300)} = \frac{1.5152}{2.0152} = 0.7519$$

$$\text{Total Proportional Taxol Effect} = \frac{250/500}{(250/500 + 5000/3300)} \times 1 = 0.2481$$

$$\text{Total Proportional Gemzar Effect} = \frac{5000/3300}{(250/500 + 5000/3300)} \times 1 = 0.7519$$

FOE1=0.2481/(0.2481+0.7519)=0.2481

FOE2=0.7519/(0.2481+0.7519)=0.7519

Calculate Taxol Dose $$\text{New Taxol Dose } (NAD1) = 250 - \left\{ \left[ \frac{\frac{(1.8-0.5) \times 0.2481}{0.5}}{1+(250/500)} \right] \times 250 \right\}$$

$$\text{New Taxol Dose } (NAD1) = 250 - \left\{ \left[ \frac{\frac{0.3225}{0.5}}{1.5} \right] \times 250 \right\}$$

New Taxol Dose (NAD1)=250−{0.4300×250}

New Taxol Dose (NAD1)=250−107.5

New Taxol Dose (NAD1)=142.5

Calculate Gemzar Dose $$\text{New Gemzar Dose } (NAD2) = 5000 - \left\{ \left[ \frac{\frac{(1.8-0.5) \times 0.7519}{0.5}}{1+(5000/3300)} \right] \times 5000 \right\}$$

$$\text{New Gemzar Dose } (NAD2) = 5000 - \left\{ \left[ \frac{1.1884}{2.5152} \right] \times 5000 \right\}$$

New Gemzar Dose (NAD2)=5000−{0.7725×5000}

New Gemzar Dose (NAD2)=5000−3862.5

New Gemzar Dose (NAD2)=1137.5

Loop Math

EANM1={[−1×(250−350)/350]×[1+(350/500)]×0.4}+0.4

Note: × by −1 because PAD1>CAD1

EANM1={[0.2857×1.7]×0.4}+0.4

EANM1={0.4857×0.4}+0.4

EANM1=0.5943

EANM2={[−1×(5000−6000)/6000]×[1+(6000/3300)]×0.5943}+0.5943

Note: × by −1 because PAD2>CAD2

EANM2={[0.1667×2.8182]×0.5943}+0.5943

EANM2={0.4698×0.5943}+0.5943

$EANM2=0.8735$ $LV1=-[RESPONSE1 \times CAD1 \times (CANM1-EANM2)/CANM1]/[1.3^{\wedge}(CAD/HIGH)]$ $LV1=-[0.2 \times 250 \times (0.6-0.8735)/0.6]/[1.3^{\wedge}(250/500)]$ $LV1=-[50 \times -0.4558]/1.1402$ $LV1=19.99$ $LV2=-[RESPONSE2 \times CAD2 \times (CANM2-EANM2)/CANM2]/[1.3^{\wedge}(CAD2/HIGH2)]$ $LV2=-[0.2 \times 5000 \times (0.6-0.8735)/0.6]/[1.3^{\wedge}(5000/3300)]$ $LV2=-[1000 \times -0.4558]/1.4882$ $LV2=306.276$

Using the IDS™ With Multi-agent (3 Agents) Therapy

When using a multi-agent regimen to treat patients it is necessary to calculate the next best dose for each agent the patient is using. The IDS™ technology in the form disclosed in applicant's U.S. Pat. No. 6,267,116 can only dose one agent at a time. The following calculations show how to use the concept of the IDS™ and the dose response methodology to perform multiple computations, each based on the proportional response which a particular agent has on the overall response that is to be achieved.

The concept underlying this multi-agent dosing model is that each agent has some contribution to the overall effect. This contribution is determined by the amount of each agent the patient is using as well as the intrinsic potency of each agent. The overall proportion of each agent is determined by the amount of agent as it relates to the dosing range. The overall proportion as well as the intrinsic potency of the agent is used to determine the total proportional effect which each agent has on the surrogate marker. This parameter (FOE1, FOE2, or FOE3) is then inserted into the four-parameter equation (AND) for calculating dose by adjusting the proportional change in marker that is attributed to the activity of the agent.

To Calculate the First Agent $NAD1=CAD1-\{[<(DANM1-CANM1) \times FOE1/CANM1>/<1+(CAD1/HIGH1)>] \times CAD1+LV1$

To Calculate the Second Agent $NAD2=CAD2-\{[<(DANM2-CANM2) \times FOE2>/<1+(CAD2/HIGH2)>] \times CAD2\}+LV2$

To Calculate the Third Agent $NAD3=CAD3-\{[<(DANM3-CANM3) \times FOE3>/<1+(CAD3/HIGH3)>] \times CAD3\}+LV3$ where:

$EANM1=\{[(CAD1-PAD1)/PAD1] \times [1+(PAD1/HIGH1)] \times PADM1\}+PADM1$ $EANM2=\{[(CAD2-PAD2)/PAD2] \times [1+(PAD2/HIGH2)] \times EANM1\}+EANM1$ $EANM3=\{[(CAD3-PAD3)/PAD3] \times [1+(PAD3/HIGH3)] \times EANM2\}+EANM2$ if CANM1<DANM1 and EANM2>CANM1, or if CANM1>DANM1 and EANM2<CANM1, then $LV1=RESPONSE1 \times CAD1 \times (EANM2-CANM1)/CANM1/[1.3^{\wedge}(CAD1/HIGH1)]$ if CANM1<DANM1 and EANM2<CANM1, or if CANM1>DANM1 and EANM2>CANM1, then $LV1=-[RESPONSE1 \times CAD1 \times (CANM1-EANM2)/CANM1]/[1.3^{\wedge}(CAD/HIGH)]$ if CANM2<DANM2 and EANM2>CANM2, or if CANM2>DANM2 and EANM2<CANM2, then $LV2=RESPONSE2 \times CAD2 \times (EANM2-CANM2)/CANM2/[1.3^{\wedge}(CAD2/HIGH2)]$ if CANM2<DANM2 and EANM2<CANM2, or if CANM2>DANM2 and EANM2>CANM2, then $LV2=-[RESPONSE2 \times CAD2 \times (CANM2-EANM2)/CANM2]/[1.3^{\wedge}(CAD2/HIGH2)]$ if CANM3<DANM3 and EANM3>CANM3, or if CANM3>DANM3 and EANM3<CANM3, then $LV3=RESPONSE3 \times CAD3 \times (EANM3-CANM3)/CANM3/[1.3^{\wedge}(CAD3/HIGH3)]$ if CANM3<DANM3 and EANM3<CANM3, or if CANM3>DANM3 and EANM3>CANM3, then $LV3=-[RESPONSE3 \times CAD3 \times (CANM3-EANM3)/CANM3]/[1.3^{\wedge}(CAD3/HIGH3)]$ PAD1=Previous agent dose of the first agent
PAD2=Previous agent dose of the second agent
PAD3=Previous agent dose of the third agent
CAD1=Current agent dose of the first agent
CAD2=Current agent dose of the second agent
CAD3=Current agent dose of the third agent
NAD1=New agent dose of the first agent
NAD2=New agent dose of the second agent
NAD3=New agent dose of the third agent
PADM1=Previous agent numerical marker for the first agent
CANM1=Current agent numerical marker for the first agent
CANM2=Current agent numerical marker for the second agent CANM3=Current agent numerical marker for the third agent DANM1=Desired agent numerical marker for the first agent DANM2=Desired agent numerical marker for the second agent DANM3=Desired agent numerical marker for the third agent FOE1=Factor of effect the first agent has on its associated numerical marker FOE2=Factor of effect the second agent has on its associated numerical marker FOE3=Factor of effect the third agent has on its associated numerical marker HIGH1=The input parameter that is the high dose range for the first agent HIGH2=The input parameter that is the high dose range for the second agent HIGH3=The input parameter that is the high dose range for the third agent RESPONSE1=Percent of total dose available for individualizing patient dose of the first agent RESPONSE2=Percent of total dose available for individualizing patient dose of the second agent RESPONSE3=Percent of total dose available for individualizing patient dose of the third agent 1.3^(CAD1/HIGH1)=1.3 raised to an exponent of (CAD1/HIGH1)

1.3^(CAD2/HIGH2)=1.3 raised to an exponent of (CAD2/HIGH2)

1.3^(CAD3/HIGH3)=1.3 raised to an exponent of (CAD3/HIGH3)

To Calculate the Proportion of Effect Based on the Amount of Agent and the Agent's Intrinsic Effect Agent1 Effect=1
Agent2 Effect=1
Agent3 Effect=1

$$Agent1\ Proportion = \frac{Dose1/Range1}{(Dose1/Range1 + Dose2/Range2 + Dose3/Range3)}$$

$$Agent2\ Proportion = \frac{Dose2/Range2}{(Dose1/Range1 + Dose2/Range2 + Dose3/Range3)}$$

$$Agent3\ Proportion = \frac{Dose3/Range3}{(Dose1/Range1 + Dose2/Range2 + Dose3/Range3)}$$

Total Proportional $Effect1 =$ $$\frac{Dose1/Range1}{(Dose1/Range1 + Dose2/Range2 + Dose3/Range3)} \times Agent1\ Effect$$

Total Proportional $Effect2 =$ $$\frac{Dose2/Range2}{(Dose1/Range1 + Dose2/Range2 + Dose3/Range3)} \times Agent2\ Effect$$

Total Proportional $Effect3 =$ $$\frac{Dose3/Range3}{(Dose1/Range1 + Dose2/Range2 + Dose3/Range3)} \times Agent3\ Effect$$

$$FOE1 = \frac{\text{Total Proportional } Effect1}{\text{Total Proportional } Effect1 + \text{Total Proportional } Effect2 + \text{Total Proportional } Effect3}$$

$$FOE2 = \frac{\text{Total Proportional } Effect2}{\text{Total Proportional } Effect1 + \text{Total Proportional } Effect2 + \text{Total Proportional } Effect3}$$

$$FOE3 = \frac{\text{Total Proportional } Effect3}{\text{Total Proportional } Effect1 + \text{Total Proportional } Effect2 + \text{Total Proportional } Effect3}$$

Using the IDS™ With Multi-agent (n Agents) Therapy

The concept underlying this multi-agent dosing model is that each agent has some contribution to the overall effect. This contribution is determined by the amount of each agent the patient is using as well as the intrinsic potency of each agent. The overall proportion of each agent is determined by the amount of agent as it relates to the dosing range. The overall proportion as well as the intrinsic potency of the agent is used to determine the total proportional effect which each agent has on the surrogate marker. This parameter (FOE1, FOE2 ... FOEn) is then inserted into the four-parameter equation (NAD1, NAD2 ... NADn) for calculating dose by adjusting the proportional change in marker that is attributed to the activity of the agent.

To Calculate the First Agent

NAD1=CAD1−{[<(DANM1−CANM1)×FOE1/CANM1>/<1+(CAD1/HIGH1)>]×CAD1+LV1

To Calculate the Second Agent

NAD2=CAD2−{[<(DANM2−CANM2)×FOE2>/<1+(CAD2/HIGH2)>]×CAD2}+LV2

To Calculate the nth Agent

NADn=CADn−{[<(DANMn−CANMn)×FOEn>/<1+(CADn/HIGHn)>]×CADn}+LVn where:

EANM1={[(CAD1−PAD1)/PAD1]×[1+(PAD1/HIGH1)]×PADM1}+PADM1

EANM2={[(CAD2−PAD2)/PAD2]×[1+(PAD2/HIGH2)]×EANM1}+EANM1

EANMn={[(CADn−PADn)/PADn]×[1+(PADn/HIGHn)]×EANM$_{n-1}$}+EANM$_{n-1}$ if CANM1<DANM1 and EANM2>CANM1, or if CANM1>DANM1 and EANM2<CANM1, then

LV1=RESPONSE1×CAD1×(EANM2−CANM1)/CANM1/[1.3^(CAD1/HIGH1)]

if CANM1<DANM1 and EANM2<CANM1, or if CANM1>DANM1 and EANM2>CANM1, then $$LV1=-[RESPONSE1 \times CAD1 \times (CANM1-EANM2)/CANM1]/[1.3\hat{\ }(CAD/HIGH)]$$

if CANM2<DANM2 and EANM2>CANM2, or
if CANM2>DANM2 and EANM2<CANM2, then $$LV2=RESPONSE2 \times CAD2 \times (EANM2-CANM2)/CANM2/[1.3\hat{\ }(CAD2/HIGH2)]$$

if CANM2<DANM2 and EANM2<CANM2, or
if CANM2>DANM2 and EANM2>CANM2, then $$LV2=-[RESPONSE2 \times CAD2 \times (CANM2-EANM2)/CANM2]/[1.3\hat{\ }(CAD2/HIGH2)]$$

...

$$LVn=RESPONSEn \times CADn \times (EANMn-CANMn)/CANMn/[1.3\hat{\ }(CADn/HIGHn)]$$

PAD1=Previous agent dose of the first agent
PAD2=Previous agent dose of the second agent
PADn=Previous agent dose of the nth agent
CAD1=Current agent dose of the first agent
CAD2=Current agent dose of the second agent
CADn=Current agent dose of the nth agent
NAD1=New agent dose of the first agent
NAD2=New agent dose of the second agent
NADn=New agent dose of the nth agent
PADM1=Previous agent numerical marker for the first agent
CANM1=Current agent numerical marker for the first agent
CANM2=Current agent numerical marker for the second agent
CANMn=Current agent numerical marker for the nth agent
DANM1=Desired agent numerical marker for the first agent
DANM2=Desired agent numerical marker for the second agent
DANMn=Desired agent numerical marker for the nth agent
FOE1=Factor of effect the first agent has on its associated numerical marker
FOE2=Factor of effect the second agent has on its associated numerical marker
FOEn=Factor of effect the nth agent has on its associated numerical marker
HIGH1=The input parameter that is the high dose range for the first agent
HIGH2=The input parameter that is the high dose range for the second agent
HIGHn=The input parameter that is the high dose range for the nth agent
RESPONSE1=Percent of total dose available for individualizing patient dose of the first agent
RESPONSE2=Percent of total dose available for individualizing patient dose of the second agent
RESPONSEn=Percent of total dose available for individualizing patient dose of the nth agent
$1.3\hat{\ }(CAD1/HIGH1)=1.3$ raised to an exponent of (CAD1/HIGH1)
$1.3\hat{\ }(CAD2/HIGH2)=1.3$ raised to an exponent of (CAD2/HIGH2)
$1.3\hat{\ }(CADn/HIGHn)=1.3$ raised to an exponent of (CADn/HIGHn)

To Calculate the Proportion of Effect Based on the Amount of Agent and the Agent's Intrinsic Effect Agent1 Effect=1
Agent2 Effect=1
Agent n Effect=1

$Agent1$ Proportion =
$$\frac{Dose1/Range1}{(Dose1/Range1 + Dose2/Range2 + \ldots Dose\,n/Range\,n)}$$

$Agent2$ Proportion =
$$\frac{Dose2/Range2}{(Dose1/Range1 + Dose2/Range2 + \ldots Dose\,n/Range\,n)}$$

$Agent\,n$ Proportion =
$$\frac{Dose\,n/Range\,n}{(Dose1/Range1 + Dose2/Range2 + \ldots Dose\,n/Range\,n)}$$

Total Proportional $Effect1$ =
$$\frac{Dose1/Range1}{(Dose1/Range1 + Dose2/Range2 + \ldots Dose\,n/Range\,n)} \times$$
$Agent1$ Effect Total Proportional $Effect2$ =
$$\frac{Dose2/Range2}{(Dose1/Range1 + Dose2/Range2 + \ldots Dose\,n/Range\,n)} \times$$
$Agent2$ Effect Total Proportional $Effect\,n$ =
$$\frac{Dose\,n/Range\,n}{(Dose1/Range1 + Dose2/Range2 + \ldots Dose\,n/Range\,n)} \times$$
$Agent\,n$ Effect $$FOE1 = \frac{\text{Total Proportional } Effect1}{\text{Total Proportional } Effect1 + \text{Total Proportional } Effect2 + \ldots \text{Total Proportional } Effect\,n}$$

$$FOE2 = \frac{\text{Total Proportional } Effect2}{\text{Total Proportional } Effect1 + \text{Total Proportional } Effect2 + \ldots \text{Total Proportional } Effect\,n}$$

$$FOEn = \frac{\text{Total Proportional } Effect\,n}{\text{Total Proportional } Effect1 + \text{Total Proportional } Effect2 + \ldots \text{Total Proportional } Effect\,n}$$

Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A method of calculating the next best dose for each agent of a multi-agent therapy which a patient may be using, comprising the steps of:
accepting as first inputs the patient's current doses of a plurality of agents which the patient may be using;
accepting as second inputs one or more numerical markers indicating one or more responses of the patient; and
calculating new agent doses for said plurality of agents as a function of said first inputs, said second inputs, and contributions each agent makes to an overall effect to be achieved by said multi-agent therapy.

2. The method according to claim 1, wherein said calculating is performed as follows:
To Calculate the First Agent $$NAD1=CAD1-\{[<(DANM1-CANM1)\times FOE1/CANM1)>/<1+(CAD1/HIGH1)>]\times CAD1\}+LV1$$

To Calculate the Second Agent $$NAD2=CAD2-\{[<(DANM2-CANM2)\times FOE2>/<1+(CAD2/HIGH2)>]\times CAD2\}+LV2$$

where:

$$EANM1=\{[(CAD1-PAD1)/PAD1]\times[1+(PAD1/HIGH1)]\times PADM1\}+PADM1$$

$$EANM2=\{[(CAD2-PAD2)/PAD2]\times[1+(PAD2/HIGH2)]\times EANM1\}+EANM1$$

if CANM1<DANM1 and EANM2>CANM1,
or
if CANM1>DANM1 and EANM2<CANM1,
then $$LV1=RESPONSE1\times CAD1\times(EANM2-CANM1)/CANM1/[1.3\hat{}(CAD1/HIGH1)]$$

if CANM1<DANM1 and EANM2<CANM1,
or
if CANM1>DANM1 and EANM2>CANM1,
then $$LV1=-[RESPONSE1\times CAD1\times(CANM1-EANM2)/CANM1]/[1.3\hat{}(CAD/HIGH)]$$

if CANM2<DANM2 and EANM2>CANM2,
or
if CANM2>DANM2 and EANM2<CANM2,
then $$LV2=RESPONSE2\times CAD2\times(EANM2-CANM2)/CANM2/[1.3\hat{}(CAD2/HIGH2)]$$

if CANM2<DANM2 and EANM2<CANM2,
or
if CANM2>DANM2 and EANM2>CANM2,
then $$LV2=-[RESPONSE2\times CAD2\times(CANM2-EANM2)/CANM2]/[1.3\hat{}(CAD2/HIGH2)]$$

PAD1=Previous agent dose of the first agent
PAD2=Previous agent dose of the second agent
CAD1=Current agent dose of the first agent
CAD2=Current agent dose of the second agent
NAD1=New agent dose of the first agent
NAD2=New agent dose of the second agent
PADM1=Previous agent numerical marker for the first agent
CANM1=Current agent numerical marker for the first agent
CANM2=Current agent numerical marker for the second agent
DANM1=Desired agent numerical marker for the first agent
DANM2=Desired agent numerical marker for the second agent
FOE1=Factor of effect the first agent has on its associated numerical marker
FOE2=Factor of effect the second agent has on its associated numerical marker
HIGH1=The input parameter that is the high dose range for the first agent
HIGH2=The input parameter that is the high dose range for the second agent
RESPONSE1=Percent of total dose available for individualizing patient dose of the first agent
RESPONSE2=Percent of total dose available for individualizing patient dose of the second agent
$1.3\hat{}(CAD1/HIGH1)=1.3$ raised to an exponent of (CAD1/HIGH1)
$1.3\hat{}(CAD2/HIGH2)=1.3$ raised to an exponent of (CAD2/HIGH2)

To Calculate the Proportion of Effect Based on the Amount of Agent and the Agent's Intrinsic Effect
Agent1 Effect=1
Agent2 Effect=1

$$Agent1\ Proportion = \frac{Dose1/Range1}{(Dose1/Range1 + Dose2/Range2)}$$

$$Agent2\ Proportion = \frac{Dose2/Range2}{(Dose1/Range1 + Dose2/Range2)}$$

Total Proportional $Effect1 =$ $$\frac{Dose1/Range1}{(Dose1/Range1 + Dose2/Range2)} \times Agent1\ \text{Effect}$$

Total Proportional $Effect2 =$ $$\frac{Dose2/Range2}{(Dose1/Range1 + Dose2/Range2)} \times Agent2\ \text{Effect}$$

$$FOE1 = \frac{\text{Total Proportional } Effect1}{\text{Total Proportional } Effect1 + \text{Total Proportional } Effect2}$$

$$FOE2 = \frac{\text{Total Proportional } Effect2}{\text{Total Proportional } Effect1 + \text{Total Proportional } Effect2}.$$

3. The method according to claim 1, wherein said calculating is performed as follows:
To Calculate the First Agent $$NAD1=CAD1-\{[<(DANM1-CANM1)\times FOE1/CANM1>/<1+(CAD1/HIGH1)>]\times CAD1\}+LV1$$

To Calculate the Second Agent $$NAD2=CAD2-\{[<(DANM2-CANM2)\times FOE2>/<1+(CAD2/HIGH2)>]\times CAD2\}+LV2$$

To Calculate the Third Agent $$NAD3=CAD3-\{[<(DANM3-CANM3)\times FOE3>/<1+(CAD3/HIGH3)>]\times CAD3\}+LV3$$

where:

$$EANM1=\{[(CAD1-PAD1)/PAD1]\times[1+(PAD1/HIGH1)]\times PADM1\}+PADM1$$

$$EANM2=\{[(CAD2-PAD2)/PAD2]\times[1+(PAD2/HIGH2)]\times EANM1\}+EANM1$$

EANM3={[(CAD3−PAD3)/PAD3]×[1+(PAD3/HIGH3)]× EANM2}+EANM2 if CANM1<DANM1 and EANM2>CANM1,
or
if CANM1>DANM1 and EANM2<CANM1,
then

LV1=RESPONSE1×CAD1×(EANM2−CANM1)/CANM1/ [1.3^(CAD1/HIGH1)]

if CANM1<DANM1 and EANM2<CANM1,
or
if CANM1>DANM1 and EANM2>CANM1,
then

LV1−[RESPONSE1×CAD1×(CANM1−EANM2)/CANM1]/ [1.3(CAD/HIGH)]

if CANM2<DANM2 and EANM2>CANM2,
or
if CANM2>DANM2 and EANM2<CANM2,
then

LV2=RESPONSE2×CAD2×(EANM2−CANM2)/CANM2/ [1.3^(CAD2/HIGH2)]

if CANM2<DANM2 and EANM2<CANM2,
or
if CANM2>DANM2 and EANM2>CANM2,
then

LV2=−[RESPONSE2×CAD2×(CANM2−EANM2)/CANM2]/ [1.3^(CAD2/HIGH2)]

if CANM3<DANM3 and EANM3>CANM3,
or
if CANM3>DANM3 and EANM3<CANM3,
then

LV3=RESPONSE3×CAD3×(EANM3−CANM3)/CANM3/ [1.3^(CAD3/HIGH3)]

if CANM3<DANM3 and EANM3<CANM3,
or
if CANM3>DANM3 and EANM3>CANM3,
then

LV3=−[RESPONSE3×CAD3×(CANM3−EANM3)/CANM3]/ [1.3^(CAD3/HIGH3)]

PAD1=Previous agent dose of the first agent
PAD2=Previous agent dose of the second agent
PAD3=Previous agent dose of the third agent
CAD1=Current agent dose of the first agent
CAD2=Current agent dose of the second agent
CAD3=Current agent dose of the third agent
NAD1=New agent dose of the first agent
NAD2=New agent dose of the second agent
NAD3=New agent dose of the third agent
PADM1=Previous agent numerical marker for the first agent
CANM1=Current agent numerical marker for the first agent
CANM2=Current agent numerical marker for the second agent
CANM3=Current agent numerical marker for the third agent
DANM1=Desired agent numerical marker for the first agent
DANM2=Desired agent numerical marker for the second agent
DANM3=Desired agent numerical marker for the third agent
FOE1=Factor of effect the first agent has on its associated numerical marker
FOE2=Factor of effect the second agent has on its associated numerical marker
FOE3=Factor of effect the third agent has on its associated numerical marker
HIGH1=The input parameter that is the high dose range for the first agent
HIGH2=The input parameter that is the high dose range for the second agent
HIGH3=The input parameter that is the high dose range for the third agent
RESPONSE1=Percent of total dose available for individualizing patient dose of the first agent
RESPONSE2=Percent of total dose available for individualizing patient dose of the second agent
RESPONSE3=Percent of total dose available for individualizing patient dose of the third agent
1.3^(CAD1/HIGH1)=1.3 raised to an exponent of (CAD1/HIGH1)
1.3^(CAD2/HIGH2)=1.3 raised to an exponent of (CAD2/HIGH2)
1.3^(CAD3/HIGH3)=1.3 raised to an exponent of (CAD3/HIGH3)

To Calculate the Proportion of Effect Based on the Amount of Agent and the Agent's Intrinsic Effect Agent1 Effect=1
Agent2 Effect=1
Agent3 Effect=1

$$Agent1 \text{ Proportion} = \frac{Dose1/Range1}{(Dose1/Range1 + Dose2/Range2 + Dose3/Range3)}$$

$$Agent2 \text{ Proportion} = \frac{Dose2/Range2}{(Dose1/Range1 + Dose2/Range2 + Dose3/Range3)}$$

$$Agent3 \text{ Proportion} = \frac{Dose3/Range3}{(Dose1/Range1 + Dose2/Range2 + Dose3/Range3)}$$

$$\text{Total Proportional } Effect1 = \frac{Dose1/Range1}{(Dose1/Range1 + Dose2/Range2 + Dose3/Range3)} \times Agent1 \text{ Effect}$$

$$\text{Total Proportional } Effect2 = \frac{Dose2/Range2}{(Dose1/Range1 + Dose2/Range2 + Dose3/Range3)} \times Agent2 \text{ Effect}$$

$$\text{Total Proportional } Effect3 = \frac{Dose3/Range3}{(Dose1/Range1 + Dose2/Range2 + Dose3/Range3)} \times Agent3 \text{ Effect}$$

$$FOE1 = \frac{\text{Total Proportional } Effect1}{\text{Total Proportional } Effect1 + \text{Total Proportional } Effect2 + \text{Total Proportional } Effect3}$$

$$FOE2 = \frac{\text{Total Proportional } Effect2}{\text{Total Proportional } Effect1 + \text{Total Proportional } Effect2 + \text{Total Proportional } Effect3}$$

$$FOE3 = \frac{\text{Total Proportional } Effect3}{\text{Total Proportional } Effect1 + \text{Total Proportional } Effect2 + \text{Total Proportional } Effect3}.$$

4. The method according to claim 1, wherein said multi-agent therapy uses n agents, and said calculating is performed as follows:

To Calculate the First Agent

NAD1=CAD1−{[<(DANM1−CANM1)×FOE1/CANM1>/<1+(CAD1/HIGH1)>]×CAD1+LV1

To Calculate the Second Agent

NAD2=CAD2−{[<(DANM2−CANM2)×FOE2>/<1+(CAD2/HIGH2)>]×CAD2}+LV2

To Calculate the nth Agent

NADn=CADn−{[<(DANMn−CANMn)×FOEn>/<1+(CADn/HIGHn)>]×CADn}+LVn where:

EANM1={[(CAD1−PAD1)/PAD1]×[1+(PAD1/HIGH1)]×PADM1}+PADM1

EANM2={[(CAD2−PAD2)/PAD2]×[1+(PAD2/HIGH2)]×EANM1}+EANM1

EANMn={[(CADn−PADn)/PADn]×[1+(PADn/HIGHn)]×EANM$_{n-1}$}+EANM$_{n-1}$ if CANM1<DANM1 and EANM2>CANM1,
or
if CANM1>DANM1 and EANM2<CANM1,
then

LV1=RESPONSE1×CAD1×(EANM2−CANM1)/CANM1/[1.3^(CAD1/HIGH1)]

if CANM1<DANM1 and EANM2<CANM1,
or
if CANM1>DANM1 and EANM2>CANM1,
then

LV1=−[RESPONSE1×CAD1×(CANM1−EANM2)/CANM1]/[1.3^(CAD/HIGH)]

if CANM2<DANM2 and EANM2>CANM2,
or
if CANM2>DANM2 and EANM2<CANM2,
then

LV2=RESPONSE2×CAD2×(EANM2−CANM2)/CANM2/[1.3^(CAD2/HIGH2)]

if CANM2<DANM2 and EANM2<CANM2,
or
if CANM2>DANM2 and EANM2>CANM2,
then

LV2−[RESPONSE2×CAD2×(CANM2−EANM2)/CANM2]/[1.3^(CAD2/HIGH2)]

. . .

LVn=RESPONSEn×CADn×(TEANM−CANMn)/CANMn/[1.3^(CADn/HIGHn)]

PAD1=Previous agent dose of the first agent
PAD2=Previous agent dose of the second agent
PADn=Previous agent dose of the nth agent
CAD1=Current agent dose of the first agent
CAD2=Current agent dose of the second agent
CADn=Current agent dose of the nth agent
NAD1=New agent dose of the first agent
NAD2=New agent dose of the second agent
NADn=New agent dose of the nth agent
PADM1=Previous agent numerical marker for the first agent
CANM1=Current agent numerical marker for the first agent
CANM2=Current agent numerical marker for the second agent
CANMn=Current agent numerical marker for the nth agent
DANM1=Desired agent numerical marker for the first agent
DANM2=Desired agent numerical marker for the second agent
DANMn=Desired agent numerical marker for the nth agent
FOE1=Factor of effect the first agent has on its associated numerical marker
FOE2=Factor of effect the second agent has on its associated numerical marker
FOEn=Factor of effect the nth agent has on its associated numerical marker
HIGH1=The input parameter that is the high dose range for the first agent
HIGH2=The input parameter that is the high dose range for the second agent
HIGHn=The input parameter that is the high dose range for the nth agent
RESPONSE1=Percent of total dose available for individualizing patient dose of the first agent
RESPONSE2=Percent of total dose available for individualizing patient dose of the second agent
RESPONSEn=Percent of total dose available for individualizing patient dose of the nth agent
1.3^(CAD1/HIGH1)=1.3 raised to an exponent of (CAD1/HIGH1)
1.3^(CAD2/HIGH2)=1.3 raised to an exponent of (CAD2/HIGH2)
1.3^(CADn/HIGHn)=1.3 raised to an exponent of (CADn/HIGHn)

To Calculate the Proportion of Effect Based on the Amount of Agent and the Agent's Intrinsic Effect Agent1 Effect=1
Agent2 Effect=1
Agent n Effect=1

$Agent1$ Proportion =

$$\frac{Dose1/Range1}{(Dose1/Range1 + Dose2/Range2 + \ldots Dose\,n/Range\,n)}$$

$Agent2$ Proportion =

$$\frac{Dose2/Range2}{(Dose1/Range1 + Dose2/Range2 + \ldots Dose\,n/Range\,n)}$$

$Agent\,n$ Proportion =

$$\frac{Dose\,n/Range\,n}{(Dose1/Range1 + Dose2/Range2 + \ldots Dose\,n/Range\,n)}$$

-continued $$\text{Total Proportional } Effect1 = \frac{Dose1/Range1}{(Dose1/Range1 + Dose2/Range2 + \ldots Dosen/Rangen)} \times Agent1 \text{ Effect}$$

$$\text{Total Proportional } Effect2 = \frac{Dose2/Range2}{(Dose1/Range1 + Dose2/Range2 + \ldots Dosen/Rangen)} \times Agent2 \text{ Effect}$$

$$\text{Total Proportional } Effectn = \frac{Dosen/Rangen}{(Dose1/Range1 + Dose2/Range2 + \ldots Dosen/Rangen)} \times Agentn \text{ Effect}$$

$$FOE1 = \frac{\text{Total Proportional } Effect1}{\text{Total Proportional } Effect1 + \text{Total Proportional } Effect2 + \ldots \text{Total Proportional } Effectn}$$

$$FOE2 = \frac{\text{Total Proportional } Effect2}{\text{Total Proportional } Effect1 + \text{Total Proportional } Effect2 + \ldots \text{Total Proportional } Effectn}$$

$$FOEn = \frac{\text{Total Proportional } Effectn}{\text{Total Proportional } Effect1 + \text{Total Proportional } Effect2 + \ldots \text{Total Proportional } Effectn}.$$

5. A storage device having stored thereon an ordered set of instructions which, when executed by a computer, performs a predetermined method, comprising:
   first means for accepting as first inputs a patient's current doses of a plurality of agents which the patient may be using in a multi-agent therapy
   second means for accepting as second inputs one or more numerical markers indicating one or more responses of the patient; and
   third means for calculating new agent doses for said plurality of agents as a function of said first inputs, said second inputs, and contributions which each agent makes to an overall effect to be achieved by said multi-agent therapy.

6. The device according to claim 5, wherein said third means calculates said new agent doses as follows:

To Calculate the First Agent

NAD1=CAD1−{[<(DANM1−CANM1)×FOE1/CANM1>/<1+(CAD1/HIGH1)>]×CAD1}+LV1

To Calculate the Second Agent

NAD2=CAD2−{[<(DANM2−CANM2)×FOE2>/<1+(CAD2/HIGH2)>]×CAD2}+LV2 where:

EANM1={[(CAD1−PAD1)/PAD1]×[1+(PAD1/HIGH1)]×PADM1}+PADM1

EANM2={[(CAD2−PAD2)/PAD2]×[1+(PAD2/HIGH2)]×EANM1}+EANM1 if CANM1<DANM1 and EANM2>CANM1,
or
if CANM1>DANM1 and EANM2<CANM1,
then

LV1=RESPONSE1×CAD1×(EANM2−CANM1)/CANM1/[1.3^(CAD1/HIGH1)]

if CANM1<DANM1 and EANM2<CANM1,
or
if CANM1>DANM1 and EANM2>CANM1,
then

LV1=−[RESPONSE1×CAD1×(CANM1−EANM2)/CANM1]/[1.3^(CAD/HIGH)]

if CANM2<DANM2 and EANM2>CANM2,
or
if CANM2>DANM2 and EANM2<CANM2,
then

LV2=RESPONSE2×CAD2×(EANM2−CANM2)/CANM2/[1.3^(CAD2/HIGH2)]

if CANM2<DANM2 and EANM2<CANM2,
or
if CANM2>DANM2 and EANM2>CANM2,
then

LV2=−[RESPONSE2×CAD2×(CANM2−EANM2)/CANM2]/[1.3^(CAD2/HIGH2)]

PAD1=Previous agent dose of the first agent
PAD2=Previous agent dose of the second agent
CAD1=Current agent dose of the first agent
CAD2=Current agent dose of the second agent
NAD1=New agent dose of the first agent
NAD2=New agent dose of the second agent
PADM1=Previous agent numerical marker for the first agent
CANM1=Current agent numerical marker for the first agent
CANM2=Current agent numerical marker for the second agent
DANM1=Desired agent numerical marker for the first agent
DANM2=Desired agent numerical marker for the second agent
FOE1=Factor of effect the first agent has on its associated numerical marker
FOE2=Factor of effect the second agent has on its associated numerical marker
HIGH1=The input parameter that is the high dose range for the first agent
HIGH2=The input parameter that is the high dose range for the second agent
RESPONSE1=Percent of total dose available for individualizing patient dose of the first agent
RESPONSE2=Percent of total dose available for individualizing patient dose of the second agent
1.3^(CAD1/HIGH1)=1.3 raised to an exponent of (CAD1/HIGH1)
1.3^(CAD2/HIGH2)=1.3 raised to an exponent of (CAD2/HIGH2)

To Calculate the Proportion of Effect Based on the Amount of Agent and the Agent's Intrinsic Effect
Agent1 Effect=1
Agent2 Effect=1

$$Agent1 \text{ Proportion} = \frac{Dose1/Range1}{(Dose1/Range1 + Dose2/Range2)}$$

$$Agent2 \text{ Proportion} = \frac{Dose2/Range2}{(Dose1/Range1 + Dose2/Range2)}$$

-continued $$\text{Total Proportional } Effect1 = \frac{Dose1/Range1}{(Dose1/Range1 + Dose2/Range2)} \times Agent1 \text{ Effect}$$

$$\text{Total Proportional } Effect2 = \frac{Dose2/Range2}{(Dose1/Range1 + Dose2/Range2)} \times Agent2 \text{ Effect}$$

$$FOE1 = \frac{\text{Total Proportional } Effect1}{\text{Total Proportional } Effect1 + \text{Total Proportional } Effect2}$$

$$FOE2 = \frac{\text{Total Proportional } Effect2}{\text{Total Proportional } Effect1 + \text{Total Proportional } Effect2}.$$

7. The device according to claim 5, wherein said third means calculates said new agent doses as follows:

To Calculate the First Agent

NAD1=CAD1-{[<(DANM1-CANM1)×FOE1/CANM1>/<1+(CAD1/HIGH1)>]×CAD1}+LV1

To Calculate the Second Agent

NAD2=CAD2-{[<(DANM2-CANM2)×FOE2>/<1+(CAD2/HIGH2)>]×CAD2}+LV2

To Calculate the Third Agent

NAD3=CAD3-{[<(DANM3-CANM3)×FOEn>/<1+(CAD3/HIGH3)>]×CAD3}+LV3 where:

EANM1={[(CAD1-PAD1)/PAD1]×[1+(PAD1/HIGH1)]×PADM1}+PADM1

EANM2={[(CAD2-PAD2)/PAD2]×[1+(PAD2/HIGH2)]×EANM1}+EANM1

EANM3={[(CAD3-PAD3)/PAD3]×[1+(PAD3/HIGH3)]×EANM2}+EANM2 if CANM1<DANM1 and EANM2>CANM1,
or
if CANM1>DANM1 and EANM2<CANM1,
then

LV1=RESPONSE1×CAD1×(EANM2-CANM1)/CANM1/[1.3^(CAD1/HIGH1)]

if CANM1<DANM1 and EANM2<CANM1,
or
if CANM1>DANM1 and EANM2>CANM1,
then

LV1-[RESPONSE1×CAD1×(CANM1-EANM2)/CANM1]/[1.3^(CAD/HIGH)]

if CANM2<DANM2 and EANM2>CANM2,
or
if CANM2>DANM2 and EANM2<CANM2,
then

LV2=RESPONSE2×CAD2×(EANM2-CANM2)/CANM2/[1.3^(CAD2/HIGH2)]

if CANM2<DANM2 and EANM2<CANM2,
or
if CANM2>DANM2 and EANM2>CANM2,
then

LV2=-[RESPONSE2×CAD2×(CANM2-EANM2)/CANM2]/[1.3^(CAD2/HIGH2)]

if CANM3<DANM3 and EANM3>CANM3,
or
if CANM3>DANM3 and EANM3<CANM3,
then

LV3=RESPONSE3×CAD3×(EANM3-CANM3)/CANM3/[1.3^(CAD3/HIGH3)]

if CANM3<DANM3 and EANM3<CANM3,
or
if CANM3>DANM3 and EANM3>CANM3,
then

LV3=-[RESPONSE3×CAD3×(CANM3-EANM3)/CANM3]/[1.3^(CAD3/HIGH3)]

PAD1=Previous agent dose of the first agent
PAD2=Previous agent dose of the second agent
PAD3=Previous agent dose of the third agent
CAD1=Current agent dose of the first agent
CAD2=Current agent dose of the second agent
CAD3=Current agent dose of the third agent
NAD1=New agent dose of the first agent
NAD2=New agent dose of the second agent
NAD3=New agent dose of the third agent
PADM1=Previous agent numerical marker for the first agent
CANM1=Current agent numerical marker for the first agent
CANM2=Current agent numerical marker for the second agent
CANM3=Current agent numerical marker for the third agent
DANM1=Desired agent numerical marker for the first agent
DANM2=Desired agent numerical marker for the second agent
DANM2=Desired agent numerical marker for the third agent
FOE1=Factor of effect the first agent has on its associated numerical marker
FOE2=Factor of effect the second agent has on its associated numerical marker
FOE3=Factor of effect the third agent has on its associated numerical marker
HIGH1=The input parameter that is the high dose range for the first agent
HIGH2=The input parameter that is the high dose range for the second agent
HIGH2=The input parameter that is the high dose range for the third agent
RESPONSE1=Percent of total dose available for individualizing patient dose of the first agent
RESPONSE2=Percent of total dose available for individualizing patient dose of the second agent
RESPONSE2=Percent of total dose available for individualizing patient dose of the third agent
1.3^(CAD1/HIGH1)=1.3 raised to an exponent of (CAD1/HIGH1)
1.3^(CAD2/HIGH2)=1.3 raised to an exponent of (CAD2/HIGH2)
1.3^(CAD3/HIGH3)=1.3 raised to an exponent of (CAD3/HIGH3)

To Calculate the Proportion of Effect Based on the Amount of Agent and the Agent's Intrinsic Effect Agent1 Effect=1
Agent2 Effect=1
Agent3 Effect=1

Agent1 Proportion =
$$\frac{Dose1/Range1}{(Dose1/Range1 + Dose2/Range2 + Dose3/Range3)}$$

Agent2 Proportion =
$$\frac{Dose2/Range2}{(Dose1/Range1 + Dose2/Range2 + Dose3/Range3)}$$

Agent3 Proportion =
$$\frac{Dose3/Range3}{(Dose1/Range1 + Dose2/Range2 + Dose3/Range3)}$$

Total Proportional $Effect1 =$
$$\frac{Dose1/Range1}{(Dose1/Range1 + Dose2/Range2 + Dose3/Range3)} \times Agent1\ \text{Effect}$$

Total Proportional $Effect2 =$
$$\frac{Dose2/Range2}{(Dose1/Range1 + Dose2/Range2 + Dose3/Range3)} \times Agent2\ \text{Effect}$$

Total Proportional $Effect3 =$
$$\frac{Dose3/Range3}{(Dose1/Range1 + Dose2/Range2 + Dose3/Range3)} \times Agent3\ \text{Effect}$$

$$FOE1 = \frac{\text{Total Proportional } Effect1}{\text{Total Proportional } Effect1 + \text{Total Proportional } Effect2 + \text{Total Proportional } Effect3}$$

$$FOE2 = \frac{\text{Total Proportional } Effect2}{\text{Total Proportional } Effect1 + \text{Total Proportional } Effect2 + \text{Total Proportional } Effect3}$$

$$FOE3 = \frac{\text{Total Proportional } Effect3}{\text{Total Proportional } Effect1 + \text{Total Proportional } Effect2 + \text{Total Proportional } Effect3}.$$

8. The device according to claim 5, wherein said multi-agent therapy uses n agents, and said third means calculates said new agent does as follows:

To Calculate the First Agent

NAD1=CAD1−{[<(DANM1−CANM1)×FOE1/CANM1>/<1+(CAD1/HIGH1>]×CAD1+LV1

To Calculate the Second Agent

NAD2=CAD2−{[<(DANM2−CANM2)×FOE2>/<1+(CAD2/HIGH2)>]×CAD2}+LV2

To Calculate the nth Agent

NADn=CADn−{[<(DANMn−CANMn)×FOEn>/<1+(CADn/HIGHn)>]×CADn}+LVn where:

EANM1={[(CAD1−PAD1)/PAD1]×[1+(PAD1/HIGH1)]×PADM1}+PADM1

EANM2={[(CAD2−PAD2)/PAD2]×[1+(PAD2/HIGH2)]×EANM1}+EANM1

EANMn={[(CADn−PADn)/PADn]×[1+(PADn/HIGHn)]×EANM$_{n-1}$}+EANM$_{n-1}$ if CANM1<DANM1 and EANM2>CANM1,
or
if CANM1>DANM1 and EANM2<CANM1,
then

LV1=RESPONSE1×CAD1×(EANM2−CANM1)/CANM1/[1.3ˆ(CAD1/HIGH1)]

if CANM1<DANM1 and EANM2<CANM1,
or
if CANM1>DANM1 and EANM2>CANM1,
then

LV1=−[RESPONSE1×CAD1×(CANM1−EANM2)/CANM1]/[1.3ˆ(CAD/HIGH)]

if CANM2<DANM2 and EANM2>CANM2,
or
if CANM2>DANM2 and EANM2<CANM2,
then

LV2=RESPONSE2×CAD2×(EANM2−CANM2)/CANM2/[1.3ˆ(CAD2/HIGH2)]

if CANM2<DANM2 and EANM2<CANM2,
or
if CANM2>DANM2 and EANM2>CANM2,
then

LV2=−[RESPONSE2×CAD2×(CANM2−EANM2)/CANM2]/[1.3ˆ(CAD2/HIGH2)

. . .

LVn=RESPONSEn×CADn×(TEANM−CANMn)/CANMn/[1.3ˆ(CADn/HIGHn)]

PAD1=Previous agent dose of the first agent
PAD2=Previous agent dose of the second agent
PADn=Previous agent dose of the nth agent
CAD1=Current agent dose of the first agent
CAD2=Current agent dose of the second agent
CADn=Current agent dose of the nth agent
NAD1=New agent dose of the first agent
NAD2=New agent dose of the second agent
NADn=New agent dose of the nth agent
PADM1=Previous agent numerical marker for the first agent
CANM1=Current agent numerical marker for the first agent
CANM2=Current agent numerical marker for the second agent
CANMn=Current agent numerical marker for the nth agent
DANM1=Desired agent numerical marker for the first agent
DANM2=Desired agent numerical marker for the second agent
DANMn=Desired agent numerical marker for the nth agent
FOE1=Factor of effect the first agent has on its associated numerical marker
FOE2=Factor of effect the second agent has on its associated numerical marker
FOEn=Factor of effect the nth agent has on its associated numerical marker
HIGH1=The input parameter that is the high dose range for the first agent
HIGH2=The input parameter that is the high dose range for the second agent
HIGHn=The input parameter that is the high dose range for the nth agent RESPONSE1=Percent of total dose available for individualizing patient dose of the first agent
RESPONSE2=Percent of total dose available for individualizing patient dose of the second agent
RESPONSEn=Percent of total dose available for individualizing patient dose of the nth agent
1.3^(CAD1/HIGH1)=1.3 raised to an exponent of (CAD1/HIGH1)
1.3^(CAD2/HIGH2)=1.3 raised to an exponent of (CAD2/HIGH2)
1.3^(CADn/HIGHn)=1.3 raised to an exponent of (CADn/HIGHn)

To Calculate the Proportion of Effect Based on the Amount of Agent and the Agent's Intrinsic Effect
Agent1 Effect=1
Agent2 Effect=1
Agent n Effect=1

$$Agent1\ Proportion = \frac{Dose1/Range1}{(Dose1/Range1 + Dose2/Range2 + \ldots Dosen/Rangen)}$$

$$Agent2\ Proportion = \frac{Dose2/Range2}{(Dose1/Range1 + Dose2/Range2 + \ldots Dosen/Rangen)}$$

$$Agentn\ Proportion = \frac{Dosen/Rangen}{(Dose1/Range1 + Dose2/Range2 + \ldots Dosen/Rangen)}$$

$$Total\ Proportional\ Effect1 = \frac{Dose1/Range1}{(Dose1/Range1 + Dose2/Range2 + \ldots Dosen/Rangen)} \times Agent1\ Effect$$

$$Total\ Proportional\ Effect2 = \frac{Dose2/Range2}{(Dose1/Range1 + Dose2/Range2 + \ldots Dosen/Rangen)} \times Agent2\ Effect$$

$$Total\ Proportional\ Effectn = \frac{Dosen/Rangen}{(Dose1/Range1 + Dose2/Range2 + \ldots Dosen/Rangen)} \times Agentn\ Effect$$

$$FOE1 = \frac{Total\ Proportional\ Effect1}{Total\ Proportional\ Effect1 + Total\ Proportional\ Effect2 + \ldots Total\ Proportional\ Effectn}$$

$$FOE2 = \frac{Total\ Proportional\ Effect2}{Total\ Proportional\ Effect1 + Total\ Proportional\ Effect2 + \ldots Total\ Proportional\ Effectn}$$

$$FOEn = \frac{Total\ Proportional\ Effectn}{Total\ Proportional\ Effect1 + Total\ Proportional\ Effect2 + \ldots Total\ Proportional\ Effectn}.$$

9. An apparatus for calculating the next best dose for each agent of a multi-agent therapy which a patient may be using, comprising:
first means for accepting as first inputs the patient's current doses of a plurality of agents which the patient may be using;
second means for accepting as second inputs one or more numerical markers indicating one or more responses of the patient; and
third means for calculating new agent doses for said plurality of agents as a function of said first inputs, said second inputs, and contributions which each agent makes to an overall effect to be achieved by said multi-agent therapy.

10. The apparatus according to claim 9, wherein said third means calculates said new agent doses as follows:

To Calculate the First Agent

NAD1=CAD1−{[<(DANM1−CANM1)×FOE1/CANM1>/<1+(CAD1/HIGH1)>]×CAD1}+LV1

To Calculate the Second Agent

NAD2=CAD2−{[<(DANM2−CANM2)×FOE2>/<1+(CAD2/HIGH2)>]×CAD2}+LV2 where:

EANM1={[(CAD1−PAD1)/PAD1]×[1+(PAD1/HIGH1)]×PADM1}+PADM1

EANM2={[(CAD2−PAD2)/PAD2]×[1+(PAD2/HIGH2)]×EANM1}+EANM1 if CANM1<DANM1 and EANM2>CANM1,
or
if CANM1>DANM1 and EANM2<CANM1,
then

LV1=RESPONSE1×CAD1×(EANM2−CANM1)/CANM1/[1.3^(CAD1/HIGH1)]

if CANM1<DANM1 and EANM2<CANM1,
or
if CANM1>DANM1 and EANM2>CANM1,
then

LV1=−[RESPONSE1×CAD1×(CANM1−EANM2)/CANM1]/[1.3^(CAD/HIGH)]

if CANM2<DANM2 and EANM2>CANM2,
or
if CANM2>DANM2 and EANM2<CANM2,
then

LV2=RESPONSE2×CAD2×(EANM2−CANM2)/CANM2/[1.3^(CAD2/HIGH2)]

if CANM2<DANM2 and EANM2<CANM2,
or
if CANM2>DANM2 and EANM2>CANM2,
then

LV2=−[RESPONSE2×CAD2×(CANM2−EANM2)/CANM2]/[1.3^(CAD2/HIGH2)]

PAD1=Previous agent dose of the first agent
PAD2=Previous agent dose of the second agent
CAD1=Current agent dose of the first agent
CAD2=Current agent dose of the second agent
NAD1=New agent dose of the first agent
NAD2=New agent dose of the second agent
PADM1=Previous agent numerical marker for the first agent
CANM1=Current agent numerical marker for the first agent
CANM2=Current agent numerical marker for the second agent
DANM1=Desired agent numerical marker for the first agent
DANM2=Desired agent numerical marker for the second agent FOE1=Factor of effect the first agent has on its associated numerical marker
FOE2=Factor of effect the second agent has on its associated numerical marker
HIGH1=The input parameter that is the high dose range for the first agent
HIGH2=The input parameter that is the high dose range for the second agent
RESPONSE1=Percent of total dose available for individualizing patient dose of the first agent
RESPONSE2=Percent of total dose available for individualizing patient dose of the second agent
1.3^(CAD1/HIGH1)=1.3 raised to an exponent of (CAD1/HIGH1)
1.3^(CAD2/HIGH2)=1.3 raised to an exponent of (CAD2/HIGH2)

To Calculate the Proportion of Effect Based on the Amount of Agent and the Agent's Intrinsic Effect
Agent1 Effect=1
Agent2 Effect=1

$$Agent1 \; Proportion = \frac{Dose1/Range1}{(Dose1/Range1 + Dose2/Range2)}$$

$$Agent2 \; Proportion = \frac{Dose2/Range2}{(Dose1/Range1 + Dose2/Range2)}$$

Total Proportional $Effect1 =$ $$\frac{Dose1/Range1}{(Dose1/Range1 + Dose2/Range2)} \times Agent1 \; Effect$$

Total Proportional $Effect2 =$ $$\frac{Dose2/Range2}{(Dose1/Range1 + Dose2/Range2)} \times Agent2 \; Effect$$

$$FOE1 = \frac{Total \; Proportional \; Effect1}{Total \; Proportional \; Effect1 + Total \; Proportional \; Effect2}$$

$$FOE2 = \frac{Total \; Proportional \; Effect2}{Total \; Proportional \; Effect1 + Total \; Proportional \; Effect2}.$$

11. The apparatus according to claim 9, wherein said third means calculates said new agent doses as follows:

To Calculate the First Agent

NAD1=CAD1−{[<(DANM1−CANM1)×FOE1/CANM1>/<1+(CAD1/HIGH1)>]×CAD1}+LV1

To Calculate the Second Agent

NAD2=CAD2−{[<(DANM2−CANM2)×FOE2>/<1+(CAD2/HIGH2)>]×CAD2}+LV2

To Calculate the Third Agent

NAD3=CAD3−{[<(DANM3−CANM3)×FOE3>/<1+(CAD3/HIGH3)>]×CAD3}+LV3 where:

EANM1={[(CAD1−PAD1)/PAD1]×[1+(PAD1/HIGH1)]×PADM1}+PADM1

EANM2={[(CAD2−PAD2)/PAD2]×[1+(PAD2/HIGH2)]×EANM1}+EANM1

EANM3={[(CAD3−PAD3)/PAD3]×[1+(PAD3/HIGH3)]×EANM2}+EANM2 if CANM1<DANM1 and EANM2>CANM1,
or
if CANM1>DANM1 and EANM2<CANM1,
then

LV1=RESPONSE1×CAD1×(EANM2−CANM1)/CANM1/[1.3^(CAD1/HIGH1)]

if CANM1<DANM1 and EANM2<CANM1,
or
if CANM1>DANM1 and EANM2>CANM1,
then

LV1=−[RESPONSE1×CAD1×(CANM1−EANM2)/CANM1]/[1.3(CAD/HIGH)]

if CANM2<DANM2 and EANM2>CANM2,
or
if CANM2>DANM2 and EANM2<CANM2,
then

LV2=RESPONSE2×CAD2×(EANM2−CANM2)/CANM2/[1.3^(CAD2/HIGH2)]

if CANM2<DANM2 and EANM2<CANM2,
or
if CANM2>DANM2 and EANM2>CANM2,
then

LV2=−[RESPONSE2×CAD2×(CANM2−EANM2)/CANM2]/[1.3^(CAD2/HIGH2)]

if CANM3<DANM3 and EANM3>CANM3,
or
if CANM3>DANM3 and EANM3<CANM3,
then

LV3=RESPONSE3×CAD3×(EANM3−CANM3)/CANM3 [1.3^(CAD3/HIGH3)]

if CANM3<DANM3 and EANM3<CANM3,
or
if CANM3>DANM3 and EANM3>CANM3,
then

LV3=−[RESPONSE3×CAD3×(CANM3−EANM3)/CANM3]/[1.3^(CAD3/HIGH3)]

PAD1=Previous agent dose of the first agent
PAD2=Previous agent dose of the second agent
PAD3=Previous agent dose of the third agent
CAD1=Current agent dose of the first agent
CAD2=Current agent dose of the second agent
CAD3=Current agent dose of the third agent
NAD1=New agent dose of the first agent
NAD2=New agent dose of the second agent
NAD3=New agent dose of the third agent
PADM1=Previous agent numerical marker for the first agent
CANM1=Current agent numerical marker for the first agent
CANM2=Current agent numerical marker for the second agent
CANM3=Current agent numerical marker for the third agent
DANM1=Desired agent numerical marker for the first agent
DANM2=Desired agent numerical marker for the second agent
DANM3=Desired agent numerical marker for the third agent
FOE1=Factor of effect the first agent has on its associated numerical marker
FOE2=Factor of effect the second agent has on its associated numerical marker FOE3=Factor of effect the third agent has on its associated numerical marker HIGH1=The input parameter that is the high dose range for the first agent HIGH2=The input parameter that is the high dose range for the second agent HIGH3=The input parameter that is the high dose range for the third agent RESPONSE1=Percent of total dose available for individualizing patient dose of the first agent RESPONSE2=Percent of total dose available for individualizing patient dose of the second agent RESPONSE3=Percent of total dose available for individualizing patient dose of the third agent $1.3^{(CAD1/HIGH1)}$=1.3 raised to an exponent of (CAD1/HIGH1)

$1.3^{(CAD2/HIGH2)}$=1.3 raised to an exponent of (CAD2/HIGH2)

$1.3^{(CAD3/HIGH3)}$=1.3 raised to an exponent of (CAD3/HIGH3)

To Calculate the Proportion of Effect Based on the Amount of Agent and the Agent's Intrinsic Effect Agent1 Effect=1
Agent2 Effect=1
Agent3 Effect=1

*Agent1* Proportion =

$$\frac{Dose1/Range1}{(Dose1/Range1 + Dose2/Range2 + Dose3/Range3)}$$

*Agent2* Proportion =

$$\frac{Dose2/Range2}{(Dose1/Range1 + Dose2/Range2 + Dose3/Range3)}$$

*Agent3* Proportion =

$$\frac{Dose3/Range3}{(Dose1/Range1 + Dose2/Range2 + Dose3/Range3)}$$

Total Proportional *Effect1* =

$$\frac{Dose1/Range1}{(Dose1/Range1 + Dose2/Range2 + Dose3/Range3)} \times Agent1 \; Effect$$

Total Proportional *Effect2* =

$$\frac{Dose2/Range2}{(Dose1/Range1 + Dose2/Range2 + Dose3/Range3)} \times Agent2 \; Effect$$

Total Proportional *Effect3* =

$$\frac{Dose3/Range3}{(Dose1/Range1 + Dose2/Range2 + Dose3/Range3)} \times Agent3 \; Effect$$

$$FOE1 = \frac{\text{Total Proportional } Effect1}{\text{Total Proportional } Effect1 + \text{Total Proportional } Effect2 + \text{Total Proportional } Effect3}$$

$$FOE2 = \frac{\text{Total Proportional } Effect2}{\text{Total Proportional } Effect1 + \text{Total Proportional } Effect2 + \text{Total Proportional } Effect3}$$

$$FOE3 = \frac{\text{Total Proportional } Effect3}{\text{Total Proportional } Effect1 + \text{Total Proportional } Effect2 + \text{Total Proportional } Effect3}.$$

12. The apparatus according to claim 9, wherein said multi-agent therapy uses n agents, and said third means calculates said new agent doses as follows:

To Calculate the First Agent

NAD1=CAD1−{[<(DANM1−CANM1)×FOE1/CANM1>/<1+(CAD1/HIGH1)>]×CAD1+LV1

To Calculate the Second Agent

NAD2=CAD2−{[<(DANM2−CANM2)×FOE2>/<1+(CAD2/HIGH2)>]×CAD2}+LV2

To Calculate the nth Agent

NADn=CADn−{[<(DANMn−CANMn)×FOEn>/<1+(CADn/HIGHn)>]×CADn}+LVn where:

EANM1={[(CAD1−PAD1)/PAD1]×[1+(PAD1/HIGH1)]×PADM1}+PADM1

EANM2={[(CAD2−PAD2)/PAD2]×[1+(PAD2/HIGH2)]×EANM1}+EANM1

EANMn={[(CADn−PADn)/PADn]×[1+(PADn/HIGHn)]×EANM$_{n-1}$}+EANM$_{n-1}$ if CANM1<DANM1 and EANM2>CANM1,
or
if CANM1>DANM1 and EANM2<CANM1,
then

LV1=RESPONSE1×CAD1×(EANM2−CANM1)/CANM1/[1.3$^{(CAD1/HIGH1)}$]

if CANM1<DANM1 and EANM2<CANM1,
or
if CANM1>DANM1 and EANM2>CANM1,
then

LV1=−[RESPONSE1×CAD1×(CANM1−EANM2)/CANM1]/[1.3$^{(CAD/HIGH)}$]

if CANM2<DANM2 and EANM2>CANM2,
or
if CANM2>DANM2 and EANM2<CANM2,
then

LV2=RESPONSE2×CAD2×(EANM2−CANM2)/CANM2/[1.3$^{(CAD2/HIGH2)}$]

if CANM2<DANM2 and EANM2<CANM2,
or
if CANM2>DANM2 and EANM2>CANM2,
then

LV2=−[RESPONSE2×CAD2×(CANM2−EANM2)/CANM2]/[1.3$^{(CAD2/HIGH2)}$]

. . .

LVn=RESPONSEn×CADn×(TEANM−CANMn)/CANMn/[1.3$^{(CADn/HIGHn)}$]

PAD1=Previous agent dose of the first agent
PAD2=Previous agent dose of the second agent
PADn=Previous agent dose of the nth agent
CAD1=Current agent dose of the first agent
CAD2=Current agent dose of the second agent
CADn=Current agent dose of the nth agent
NAD1=New agent dose of the first agent
NAD2=New agent dose of the second agent
NADn=New agent dose of the nth agent
PADM1=Previous agent numerical marker for the first agent
CANM1=Current agent numerical marker for the first agent CANM2=Current agent numerical marker for the second agent
CANMn=Current agent numerical marker for the nth agent
DANM1=Desired agent numerical marker for the first agent
DANM2=Desired agent numerical marker for the second agent
DANMn=Desired agent numerical marker for the nth agent
FOE1=Factor of effect the first agent has on its associated numerical marker
FOE2=Factor of effect the second agent has on its associated numerical marker
FOEn=Factor of effect the nth agent has on its associated numerical marker
HIGH1=The input parameter that is the high dose range for the first agent
HIGH2=The input parameter that is the high dose range for the second agent
HIGHn=The input parameter that is the high dose range for the nth agent
RESPONSE1=Percent of total dose available for individualizing patient dose of the first agent
RESPONSE2=Percent of total dose available for individualizing patient dose of the second agent
RESPONSEn=Percent of total dose available for individualizing patient dose of the nth agent
1.3^(CAD1/HIGH1)=1.3 raised to an exponent of (CAD1/HIGH1)
1.3^(CAD2/HIGH2)=1.3 raised to an exponent of (CAD2/HIGH2)
1.3^(CADn/HIGHn)=1.3 raised to an exponent of (CADn/HIGHn)

To Calculate the Proportion of Effect Based on the Amount of Agent and the Agent's Intrinsic Effect Agent1 Effect=1
Agent2 Effect=1
Agent n Effect=1

$Agent1\ \text{Proportion} = \dfrac{Dose1/Range1}{(Dose1/Range1 + Dose2/Range2 + \ldots Dose\,n/Range\,n)}$ $Agent2\ \text{Proportion} = \dfrac{Dose2/Range2}{(Dose1/Range1 + Dose2/Range2 + \ldots Dose\,n/Range\,n)}$ $Agent\,n\ \text{Proportion} = \dfrac{Dose\,n/Range\,n}{(Dose1/Range1 + Dose2/Range2 + \ldots Dose\,n/Range\,n)}$ Total Proportional $Effect1 =$ $\dfrac{Dose1/Range1}{(Dose1/Range1 + Dose2/Range2 + \ldots Dose\,n/Range\,n)} \times Agent1\ \text{Effect}$ Total Proportional $Effect2 =$ $\dfrac{Dose2/Range2}{(Dose1/Range1 + Dose2/Range2 + \ldots Dose\,n/Range\,n)} \times Agent2\ \text{Effect}$ Total Proportional $Effect\,n =$ $\dfrac{Dose\,n/Range\,n}{(Dose1/Range1 + Dose2/Range2 + \ldots Dose\,n/Range\,n)} \times Agent\,n\ \text{Effect}$ $FOE1 = \dfrac{\text{Total Proportional}\ Effect1}{\text{Total Proportional}\ Effect1 + \text{Total Proportional}\ Effect2 + \ldots \text{Total Proportional}\ Effect\,n}$ $FOE2 = \dfrac{\text{Total Proportional}\ Effect2}{\text{Total Proportional}\ Effect1 + \text{Total Proportional}\ Effect2 + \ldots \text{Total Proportional}\ Effect\,n}$ $FOEn = \dfrac{\text{Total Proportional}\ Effect\,n}{\text{Total Proportional}\ Effect1 + \text{Total Proportional}\ Effect2 + \ldots \text{Total Proportional}\ Effect\,n}$.

* * * * *